Figure 1:
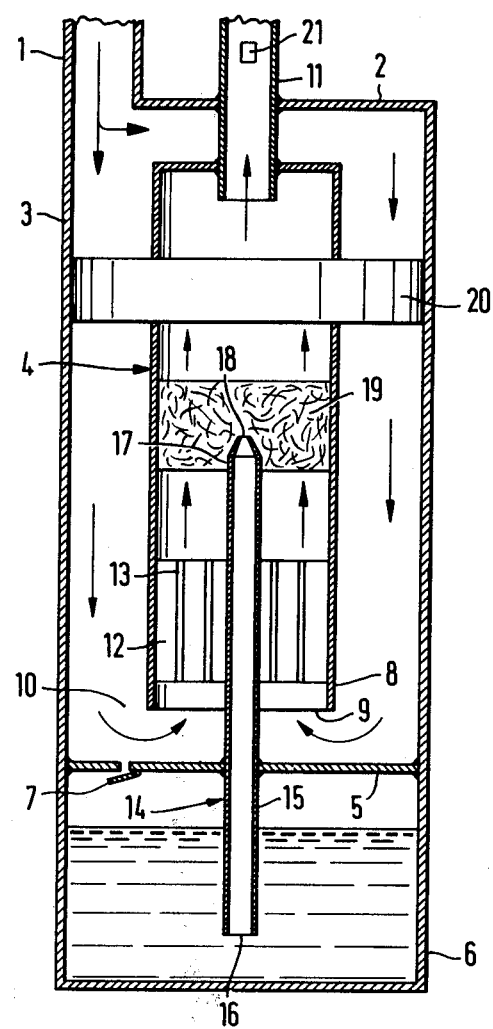

United States Patent [19]

Ottestad

[11] 4,288,396

[45] Sep. 8, 1981

[54] METHOD AND DEVICE FOR CONDITIONING OF BREATHING AIR FOR DIVERS

[76] Inventor: Nils T. Ottestad, Hilton 156 A, N-2040 Kløfta, Norway

[21] Appl. No.: 116,414

[22] Filed: Jan. 29, 1980

Related U.S. Application Data

[63] Continuation of Ser. No. 961,826, Nov. 17, 1978, abandoned.

[51] Int. Cl.³ .............................................. B01F 3/04
[52] U.S. Cl. ............................... 261/128; 128/203.27;
128/204.13; 128/204.14; 128/204.17; 219/274;
261/65; 261/99; 261/107; 261/119 R; 261/129;
261/142; 261/DIG. 65; 405/185
[58] Field of Search ............... 261/99, 104, 107, 78 A,
261/128-130, 142, 152, 158-161, DIG. 48,
DIG. 65, DIG. 77, 65; 128/142.2, 142.3, 186,
192, 193, 203.27, 204.13-204.17; 219/271-276;
405/185, 186

[56] References Cited

U.S. PATENT DOCUMENTS

| B 403,507 | 2/1976 | Robinson | 261/DIG. 65 |
|---|---|---|---|
| 1,072,133 | 9/1913 | Lyle | 261/161 |
| 2,921,776 | 1/1960 | Keeping | 261/DIG. 72 |
| 3,128,739 | 4/1964 | Schultz | 405/185 X |
| 3,332,672 | 7/1967 | Schipper | 261/129 |
| 3,358,413 | 12/1967 | Kalika | 261/161 X |
| 3,735,568 | 5/1973 | Beck | 261/160 X |
| 3,836,129 | 9/1974 | Perelmutr et al. | 261/DIG. 65 |
| 3,954,920 | 5/1976 | Heath | 261/DIG. 65 |
| 4,014,382 | 3/1977 | Heath | 261/DIG. 65 |
| 4,051,205 | 9/1977 | Grant | 261/DIG. 65 |

Primary Examiner—Richard L. Chiesa
Attorney, Agent, or Firm—Sughrue, Mion, Zinn, Macpeak and Seas

[57] ABSTRACT

There is disclosed a method and a device for conditioning of heated breathing air for divers.

Breathing air supplied from compressed air containers through pressure reducing valves is very cold and dry. Heating of breathing air makes the air even drier and, due to the low specific heat of air it cannot supply the diver with a substantial amount of heat.

According to the invention the air is heated to above the body temperature of the diver and humidified to close to saturation. Upon inhalation the air temperature is lowered whereby some of the vapor will condense and give off its heat of evaporation. The device according to the invention contains air passages wherein the air is heated, humidified by means of wicks or a tube provided with a nozzle arranged in a Venturi portion connected to a water tank, and an air temperature regulating device.

5 Claims, 2 Drawing Figures

METHOD AND DEVICE FOR CONDITIONING OF BREATHING AIR FOR DIVERS

This is a Continuation of application Ser. No. 961,826, filed Nov. 17, 1978 now abandoned.

The invention relates to a method and a device for conditioning of breathing air for divers.

For maintainance of the body temperature of a person it is necessary that the heat per unit of time developed by the body or supplied thereto corresponds to the energy per unit of time given off to the surroundings of the person. The giving off or delivery to the surroundings takes place in breathing out humid gases heated by the body, heat transfer from the body by conduction, radiation and convection of heat, and mechanical work carried out by the person.

Thus, warming of persons in order to prevent lowering of the body temperature, or in order to raise this can be carried out by supplying heat energy or preventing heat delivery to the surroundings.

In order to prevent heat loss to the surroundings, it is known to use isolating suits, so-called frogman's suits, but these cannot prevent that divers feed cold after staying for some time in the sea. It has therefore been necessary to supply heat, which has been done by introducing warm water between the body of the diver and the isolating suit, which warm water, however, may cause washing out of the skin and promote growth of micro organisms, such as fungus or the like, on the skin. It is also known to introduce warm water through passages in a diver's suit.

The breathing air of divers has also been used as heat carrier. In the known portable compressed air devices, in which compressed air at ambient temperature flows from compressed air bottles to the diver through reducing valves, in order to adjust the pressure of the breathing air to the ambient pressure, the breathing air will be cold, due to the pressure reduction. The air, however, must be dry in order to prevent formation of ice in the valves, and upon possible heating of the air to above body temperature, e.g. after pressure reduction, its relative humidity will be small, which promotes drying of the mucous membranes in the tracheas. Due to the low specific heat of air, however, the breathing air must be very warm and it therefore becomes very dry. In practice, however, it has proved to be impossible to supply the diver with so much heat per unit of time by means of such heated air alone, that hedoes not feel cold.

The purpose of the invention is to provide a method and a device for conditioning of breathing air for divers, which method and device eliminates the above-mentioned drawbacks in use of heated breathing air.

The characteristic feature of the method according to the invention is that the breathing air, which is heated to above the body temperature of the user, is humidified to close to saturation, so that its temperature is lower than the dew point when it is cooled in the tracheas. Hereby a part of the vapor contents of the air is condensed. The heat released during the condensation is given off to the body and the condensate is absorbed by the lung tissue and the blood.

Assuming that the heat per unit of time corresponding to the mechanical work performed by the body, and the heat per unit of time given off by the body to the surroundings by conduction, radiation and convection of heat is constant, that the air exhalation is approximately at body temperature and approximately saturated with vapor, and that the heat per unit of time produced by the body itself is constant, the body temperature may be influenced by controlling the temperature and humidity of the breathing air.

The characteristic features of the device according to the invention will be evident from the claims.

Figure 2:
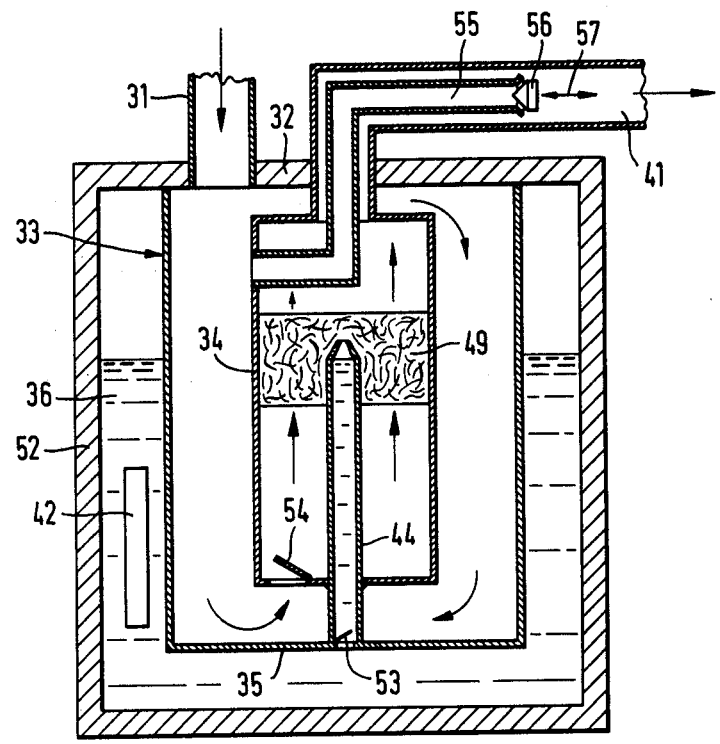

The invention will be described in detail in the following description with reference to the accompanying drawings, in which:

FIGS. 1 and 2 are schematic longitudinal sections of two embodiments of a device according to the invention.

The device shown in FIG. 1 comprises an elongated, tubular housing 3 with an upper cross wall 2 and a lower cross wall 5. The upper cross wall 2 is provided with an inlet tube 1 connected to a not shown compressed air tank or compressor through a not shown pressure reducing valve, and the lower cross wall 5 forms an upper portion of a water container 6 fastened to the lower end of the housing 3. The cross wall 5 is provided with a flap valve 7 which is spring loaded to closed position and which opens in the direction towards the container 6. Centrally in the housing 3 there is arranged an inner tube 4 of which the upper end portion, which constitutes the outlet tube 11 of the device, is carried through the upper cross wall 2 of the housing 3, and of which the lower end portion 8 is arranged with its opening 9 at some distance above the wall 5, thereby forming a slot 10 connecting the space between the housing 3 and the central tube 4 with the inner portion thereof.

In the lower end of the central tube 4 there is arranged an e.g. electrical heating element 12, and above this a filter-like plug 19 made of metal threads, thin metal strips etc. reducing the cross-section of the tube 4.

A tube 14 with small diameter and co-axially arranged in relation to the tube 4 extends through and is fastened to the lower cross wall 5 of the housing 3. The lower end portion 15 of the tube 14 has an inlet opening 16 arranged at a distance above the bottom of the water container 6. The tube 14 extends upwards through a bore in the heating element 12 and its upper end portin 17 has an outlet opening 18 arranged in the filter-like plug 19.

A heat exchanger 20 extending in the transverse direction of the housing 3 and the tube 4, is arranged above the filter-like plug 19. In the heat exchanger there are formed throughgoing openings extending in the longitudinal direction of the housing 3 and the tube 4.

In the outlet tube 11 of the tube 4 there is arranged a temperature sensor 21 which is operatively connected to the heating element 12 for controlling the output thereof. The outlet tube 11 may be connected to the diver's mouth through e.g. a further, not shown reducing valve.

As in the above described embodiment of the device according to the invention, the embodiment shown in FIG. 2 comprises an elongated, tubular housing 33 provided with a lower cross wall 35. The housing is enclosed by a mantle 52, the space therebetween and the housing 33 being adapted to be filled with water through a not shown filler pipe, and the mantle 52 thereby constituting the water container 36 of the device.

The upper cross wall 32 of the mantle 52 constitutes the roof or the upper cross wall of the housing 33 through which wall the inlet tube 31 of the housing extends.

Centrally in the housing 33, e.g. co-axially in relation thereto, there is arranged an inner tube 34 of which the upper end portion, which constitutes the outlet tube 41 of the device, is extended through the upper cross wall 32 of the mantle 52. The lower end portion of the inner tube 34 is provided with a cross wall, in which there is arranged a spring loaded flap valve 54, which opens upwards in the direction away from the lower portion of the housing 33, into the inner tube 34. A tube 44 extends co-axially in relation to the tubular housing 33 from and opening formed in the lower cross wall thereof and up into the inner tube 34, the upper end of the tube 44 being provided with a nozzle and terminated and enclosed by a filter-like plug 49 filling the whole cross-section of the inner tube 34.

In the lower end portion of the nozzle tube 44 there may be arranged a spring loaded flap valve 53 opening, i.e. permitting fluid flow, upwards towards the nozzle. A heating element 42 is arranged in the water container 36, which element is adapted to maintain constant temperature of the water.

A cooling tube 55, one end of which is carried through the wall of the outlet tube 41 inside the housing 33, is extending inside the outlet tube 41 along part of the length and in the downstream direction thereof. In its other end the cooling tube 55 is provided with a valve body 56, adapted to open and close this end depending on the temperature of the breathing air which flows in the outlet tube, as indicated by the arrows 57, e.g. by means of a bimetallic spring or the like.

In addition to the above-mentioned valves, both embodiments may be provided with not shown valves for full or partial mutual compensation of pressure between the various spaces of the device and/or between these spaces and the surrounding water during e.g. rise or descent in the sea, for the return of condensed vapor back to the water container, and to provide bypass of breathing air past the inner tube 34 if e.g. the filter-like plug 49 should become clogged.

The function of the embodiment illustrated in FIG. 1 is as follows.

Dry, cold air from a compressed air container, compressor or the like, flows into the inlet tube 1 of the device through a reducing valve as a consequence of a pressure reduction at the outlet tube 11 caused by inhalation of the diver. Dry air with a pressure somewhat higher than the ambient pressure flows downwards in the space formed between the inner tube 4 and the housing 3, through the openings in the part of the heat exchanger 20 being arranged in this space, whereby the air is somewhat heated. At the lower end of the housing 3 the air flow is deflected and guided through the slot 10 formed between the lower end portion 8 of the inner tube 4 and the lower cross wall 5 of the housing 3, and upwards into the inner tube 4, through the openings 13 of the heating element 12, where the temperature of the air is raised to e.g. above 100° C.

The filter-like plug 19 which forms a reduction of the cross-section of the tube 4 causes acceleration of the air flow with a consequent reduction of the static pressure thereof, similar to a Venturi nozzle, when the diver inhalates. This causes water to be sucked upwards through the tube 14 from the water container 6, which water is then distributed in the plug 19 on the threads or strips thereof, whereby the effective evaporating surface becomes large. The valve 7 opens when the difference between the pressure of the air above the cross wall 5 and the pressure of the air above the water in the container 6 reaches a predetermined value.

The water in the plug 19 is heated by the hot air and evaporates, whereby the temperature of the air falls to e.g. 80° C.–100° C., while the relative humidity rises to e.g. 50%. The air then flows past the heat exchanger 20, whose portion being positioned outside the tube 4 is cooled by the cold air flowing in the inlet tube 1, and the temperature of the air is lowered to e.g. 50° C., while the relative humidity is raised substantially. The air then flows out of the outlet tube 11, past the temperature sensor 21 arranged therein, which, e.g. through a per se known electronic circuit, controls the output delivered by the heating element and thus provides the diver with air of a suitable temperature through a reducing valve which reduces the air pressure to approximately ambient pressure. Due to the fact that the dry, cold air is flowing on the outside of the inner tube 4, through which warm air is flowing along a large portion of its length, the heat loss of the device to the surroundings is reduced.

If desired the device may be isolated in order to obtain further reduction of the heat loss.

The device shown in FIG. 2 operates in a similar way.

When the pressure in the outlet tube 41 is lowered due to inhalation, dry, cool air will flow from the compressed air container, compressor or the like, through a reducing valve, into the inlet tube 31 of the device and downwards into the space formed between the housing 33 and the inner tube 34. The water contained in the water container 36 and heated by the heating element 42 will deliver some of its heat through the walls of the housing 33 to the air flowing in said space, and the thus heated, very dry air will flow into the inner tube 34 through the valve 54. Here water will be sucked up into the nozzle tube 44 in the same way as described above and moisten the air which flows out of the outlet tube 41. If the temperature of the breathing air flowing in the outlet tube 41 is too high, a device, e.g. a bimetallic spring or the like, which acts upon the valve body 56, will move this away from its seat and thereby cause opening of the outlet end of the cooling tube 55, whereby cold air will flow from the inlet of the device, through the cooling tube and cool this and thereby the surrounding breathing air in the outlet tube 41. The cold air eventually flows out into this tube, past the valve body 56. If the temperature of the breathing air thereby should become too low, the valve body will close the outlet end of the cooling tube.

Instead of the tube 14 or 44 and the filter-like plug 19 or 49, there may be arranged wicks drawing water from the water container 6 or 36 and introducing the water into the inner tube 4 or 34, downstream of the portion of the air flow passage which is influenced by the heating element for supplying water to the heated, dry air.

What I claim is:

1. A method of conditioning the breathing air for an underwater diver, comprising: the steps of drawing dry, cold air from a source of pressurized air located underwater and being connected to a conditioning apparatus located underwater, in response to the breathing demand of the diver, heating said air in said apparatus to a temperature substantially higher than the body temperature of the diver; humidifying said heated air by supplying water thereto and passing it through a filter means having a large surface wherein said water is distributed over said surface for achieving efficient vaporization; and cooling the heated and humidified air to a temperature slightly above the body temperature of the diver and thereby increasing the relative humidity of said air to close to saturation, and supplying the so-conditioned air as breathing air directly to the lungs of the diver.

2. Apparatus for conditioning breathing air for an underwater diver, said apparatus being located underwater, comprising:

(a) a housing defining an air passage therethrough;

(b) an inlet tube coupled to one end of said air passage for connection to a supply of pressurized, dry, cold air;

(c) a heating element for heating the dry, cold air arriving at and passing said air passage;

(d) a container located adjacent to said air passage for holding a supply of water;

(e) means for controllably supplying humidifying water from said container to the heated air;

said means comprising a metal filter gauze having a large surface for effecting distribution and efficient vaporization of water supplied thereto together with said heated air;

(f) an outlet tube coupled to another end of said air passage for connection to means including a breathing valve control for supplying air conditioned by the apparatus to the driver; and (g) temperature sensing means within the apparatus and at said breathing valve control arranged to control means for regulating the temperature of the breathing air so that the conditioned breathing air has a temperature slightly above the body temperature of the diver and a relative humidity close to saturation.

3. Apparatus according to claim 2, wherein said metal filter gauze constitutes a constricted portion of said air passage, said constricted portion being located directly downstream from a portion of the air passage heated by said heating element, and a tube connecting said constricted portion with water in said container.

4. Apparatus according to claims 2 or 3, further comprising a heat exchanger arranged downstream of the heating element and the place at which water is supplied to the heated air for preheating the arriving dry, cold air and cooling the heated and humidified air.

5. Apparatus according to claims 2 or 3, further comprising a cooling tube extending within a portion of said outlet tube, said cooling tube having an inlet opening communicating with said inlet tube and an outlet opening within the outlet tube, said outlet opening being controlled by said temperature regulating means.

* * * * *